United States Patent
Schlender et al.

(10) Patent No.: US 11,679,054 B2
(45) Date of Patent: Jun. 20, 2023

(54) USER-CUSTOMIZED DELIVERY OF STREAMED MULTI-SENSORY MEDIA TO A VIBROACOUSTIC THERAPY BED

(71) Applicant: Opus Immersive, Inc., Austin, TX (US)

(72) Inventors: Adam Schlender, Austin, TX (US); Christopher Schenk, Austin, TX (US)

(73) Assignee: OPUS IMMERSIVE, INC., Austin, TX (US)

( * ) Notice: Subject to any disclaimer, the term of this patent is extended or adjusted under 35 U.S.C. 154(b) by 69 days.

(21) Appl. No.: 17/326,943

(22) Filed: May 21, 2021

(65) Prior Publication Data
US 2022/0370278 A1 Nov. 24, 2022

(51) Int. Cl.
*A61H 1/00* (2006.01)
*A61M 21/00* (2006.01)
*G16H 20/30* (2018.01)

(52) U.S. Cl.
CPC ............. *A61H 1/005* (2013.01); *A61M 21/00* (2013.01); *G16H 20/30* (2018.01); *A61H 2201/0142* (2013.01); *A61H 2201/5007* (2013.01); *A61M 2021/0022* (2013.01); *A61M 2021/0027* (2013.01); *A61M 2021/0044* (2013.01); *A61M 2205/50* (2013.01)

(58) Field of Classification Search
CPC .............................................. A61M 21/00–02
See application file for complete search history.

(56) References Cited

U.S. PATENT DOCUMENTS

| | | | |
|---|---|---|---|
| 6,369,312 B1 | 4/2002 | Komatsu |
| 6,702,767 B1 | 3/2004 | Douglas |
| 8,517,911 B1 | 8/2013 | Thompson |
| 10,737,054 B1 | 8/2020 | Lynn |
| 2003/0074227 A1 | 4/2003 | Yu |
| 2008/0208284 A1 | 8/2008 | Rezai |
| 2010/0320819 A1 | 12/2010 | Cohen |
| 2011/0237989 A1 | 9/2011 | Vandenbelt |
| 2011/0245586 A1 | 10/2011 | Slane |
| 2011/0251535 A1 | 10/2011 | Bender |
| 2013/0263370 A1 | 10/2013 | Giese |

(Continued)

OTHER PUBLICATIONS

International Search Report and Written Opinion in PCT/US2022/022003 dated Aug. 1, 2022.
(Continued)

*Primary Examiner* — Thaddeus B Cox
(74) *Attorney, Agent, or Firm* — Amsel IP Law PLLC; Jason Amsel

(57) ABSTRACT

A multi-sensory media experience delivery platform includes a vibroacoustic therapy bed that delivers a multi-sensory media experience locally stored, streaming, on-demand, or real-time signals. The vibroacoustic therapy bed drives a plurality of sensory output devices based on a set of sensory output channels to produce sounds, vibrations, light patterns, or other sensory outputs. The channels may be derived from dedicated signals created for a specific sensory output device or may be derived from an audio file or other general set of waveforms. The multi-sensory media experience may be customized to a user based on user profile data, metadata associated with the multi-sensory media experience, or biometric data. Furthermore, users can create customized multi-sensory media experiences from libraries of sounds or other media.

20 Claims, 11 Drawing Sheets

(56) References Cited

U.S. PATENT DOCUMENTS

2020/0188629 A1   6/2020 Levenberg
2021/0010978 A1   1/2021 Johanneson
2022/0117401 A1   4/2022 Wang

OTHER PUBLICATIONS

Kantor et al. "Potential of Vibroacoustic Therapy in Persons with Cerebral Palsy: An Advanced Narrative Review", MDPI, Int J Environ Res Public Health, 2019. Retrieved on Jul. 7, 2022, from <URL: https://www.ncbi.nlm.nih.gov/pmc/articles/PMC6843730/>.

Office Action (Non-Final Rejection) dated Jan. 19, 2023 for U.S. Appl. No. 17/326,975 (pp. 1-12).

USER-CUSTOMIZED DELIVERY OF STREAMED MULTI-SENSORY MEDIA TO A VIBROACOUSTIC THERAPY BED

BACKGROUND

Technical Field

This application relates generally to a vibroacoustic therapy bed, and more specifically, to delivery of a multi-sensory media experience using a vibroacoustic therapy bed.

Description of Related Art

A vibroacoustic therapy bed includes a set of transducers that transfer vibrations to the body according to a programmed pattern. These vibration effects can provide health benefits such as increasing circulation, relieving pain, and improving mood. However, conventional vibroacoustic therapy beds have limited capabilities, thereby constraining the benefits they can provide to diverse users with varying needs.

DETAILED DESCRIPTION

The Figures (FIGS.) and the following description describe certain embodiments by way of illustration only. One skilled in the art will readily recognize from the following description that alternative embodiments of the structures and methods illustrated herein may be employed without departing from the principles described herein. Reference will now be made to several embodiments, examples of which are illustrated in the accompanying figures. It is noted that wherever practicable similar or like reference numbers may be used in the figures and may indicate similar or like functionality.

Figure 1A:
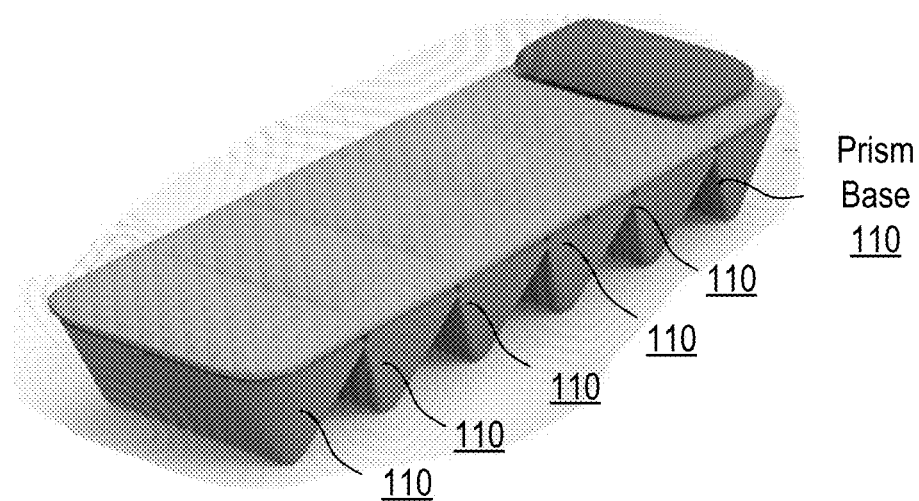
FIG. 1A is first view of an example embodiment of a vibroacoustic therapy bed.
Figure 1B:
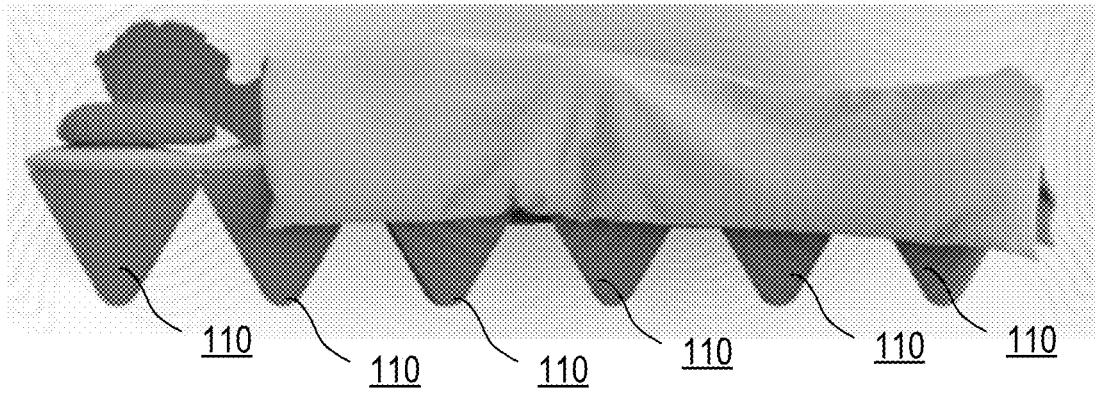
FIG. 1B is second view of an example embodiment of a vibroacoustic therapy bed.

FIGS. 1A-1B illustrate an example embodiment of a vibroacoustic therapy bed 100 for delivering a multi-sensory media experience. The vibroacoustic therapy bed 100 includes integrated electronics for providing sensory outputs such as vibrations, sounds, lights, or other effects. For example, the integrated electronics may include speakers, vibrational transducers, light emitting devices (LEDs) or other output devices that operate in combination to deliver the multi-sensory media experience. The integrated electronics may furthermore include integrated biometric sensors for sensing conditions of the user such as weight, heart rate, blood pressure, breathing pattern, temperature, audible voice, or other conditions. The multi-sensory experience may be controlled locally (e.g., according to an experience file that specifies a pattern of effects outputted by the vibroacoustic therapy bed 100) or may be controlled remotely via a digital communication link (e.g., as a streaming experience that may be accessed on-demand or streamed in real-time as it is created). Furthermore, the multi-sensory media experience may be customized to a user based on the user's individual profile or based on real-time biometric data associated with the user.

In an embodiment, the vibroacoustic therapy bed 100 comprises a series of base elements 110 (e.g., prisms) connected together to form a platform. The base elements 110 may be detachable from each other to enable a modular construction. Base elements 110 can be added or removed to create beds 100 of varying length or to enable different capabilities dependent on the style of base elements 110 being coupled together. In some configurations of a vibroacoustic therapy bed 100, the base elements 110 may each be substantially identical. In other configurations, different base elements 110 may include different capabilities. For example, in one architecture, some base elements 110 deliver vibration outputs while others produce light patterns during a multi-sensory media experience. In other configurations, each of the base elements 110 include vibratory transducers of varying type. For example, some of the base elements 110 may include low frequency transducers while other base elements 110 may include mid-frequency or high-frequency transducers that deliver vibrations in different frequency ranges. In a particular example configuration, the base element 110 positioned near the head is specially configured to provide audio outputs and to act as a master controller for the vibroacoustic therapy bed 100, while the remaining set of base elements 110 are identically configured to each include one or more vibratory transducers and/or one or more lighting systems.

Figure 2:
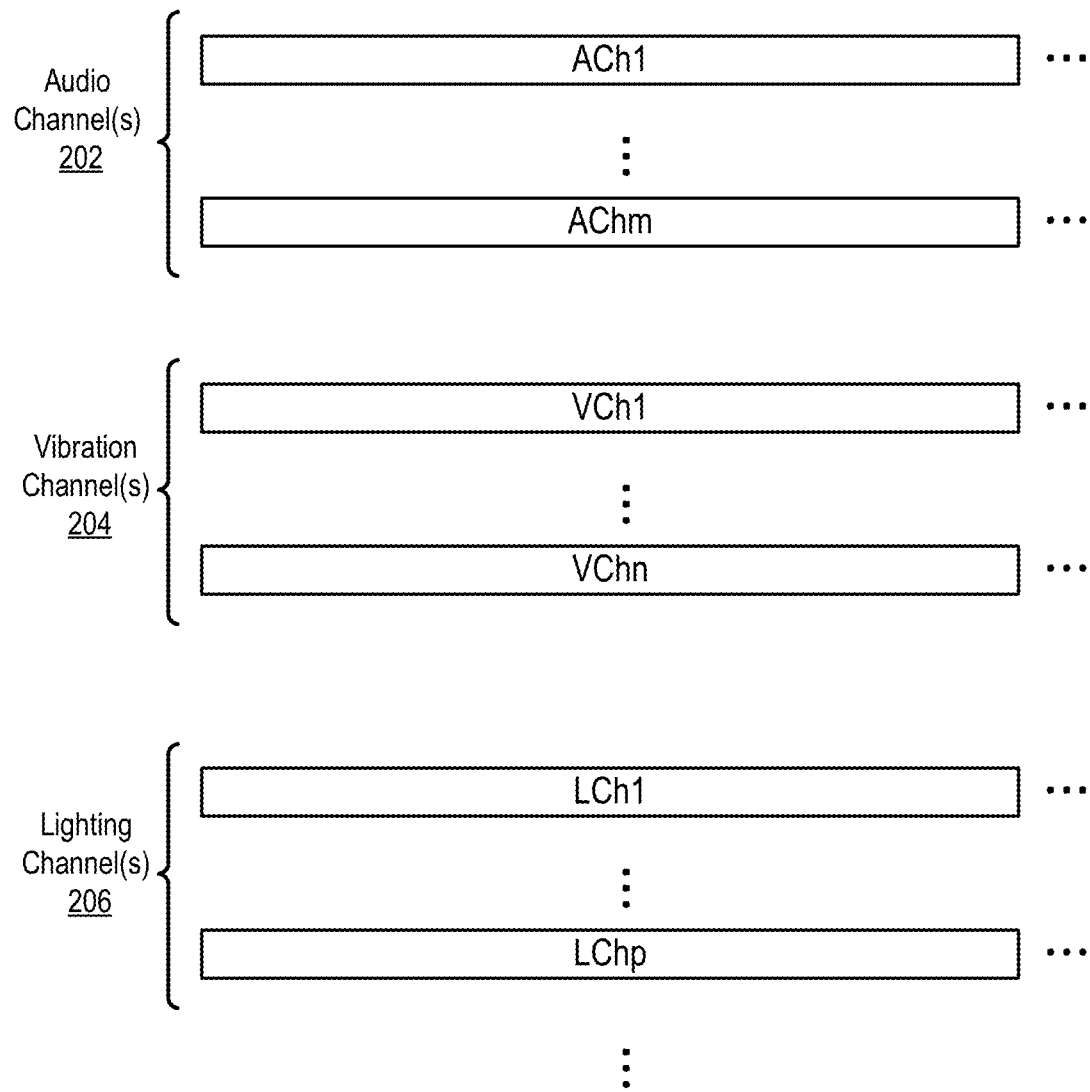
FIG. 2 is an example embodiment of a multi-sensory media experience format.

FIG. 2 illustrates an example structure of a multi-sensory media experience file 200 that can be executed by the vibroacoustic therapy bed 100 to deliver a multi-sensory media experience. The multi-sensory media experience file 200 comprises a plurality of channels that may be of different types including one or more audio channels 202, one or more vibration channels 204, and one or more lighting channels 206. Each channel drives one or more sensory output device (e.g., audio speakers, vibrational transducers, lighting systems, etc.) and specifies the relative timing, intensity, frequency, and other parameters of the sensory outputs delivered by each of the output devices. For example, the vibroacoustic therapy bed 100 may deliver a combination of audio (music and/or sound clips) via the audio channels 202, vibrations via the vibration channels 204, and lighting patterns via the lighting channels 206, to speakers, vibrational transducers, and lighting systems respectively that are integrated at different locations in the vibroacoustic therapy bed 100.

In some multi-sensory media experiences, the audio channels 202 and vibration channels 204 may be generated from the same underlying signal (or set of signals). Here, the vibrational transducers operate similarly to a speaker to vibrate in response to a waveform, except that the transducers are physically designed to optimize transfer of vibrational energy to a localized area (e.g., a body part of the user) while the speakers are designed to optimize production of sound waves in the air. In this case, one or more vibration channels 204 may be identical to one or more of the audio channels 202, or they may otherwise be derived from the same underlying set of waveforms.

The lighting channels 206 may similarly be related to the audio channels 202 and/or the vibration channels 204. For example, the lighting channels 206 may be generated by processing an audio signal to extract certain features used to control timing of the light patterns. In one implementation, an audio waveform may be processed to detect a beat in the music (e.g., a bass drum beat) and the vibroacoustic therapy bed 100 may generate the lighting channels 206 to synchronize turning on or off of LEDs to the timing of the beat. In another example, an audio waveform may be processed to detect individual notes of a melody and the vibroacoustic therapy bed 100 may generate the lighting channels 206 to synchronize turning LEDs on or off based on the timing of the note changes in the melody. In some such embodiments, the audio channels 202, vibration channels 204, and lighting channels 206 are not necessarily distinct. Instead, a combined channel may be used to drive two or more different types of sensory output devices using the same waveforms. For example, a combined channel may drive all of the output devices (e.g., one or more vibrational transducers and/or one or more lighting systems) of each base element 110.

In other multi-sensory media experiences, the vibration channels 204 or light channels 206 may be independent of the audio channels 202 and each other. Thus, for example, a multi-sensory media experience file 200 could include audio channels 202 for playing an audio track, vibration channels 204 for generating vibrations based on a dedicated waveform (or set of waveforms) that is independent of the audio track, and lighting channels 206 for generating lighting patterns based on a different dedicated waveform (or set of waveforms) that may be independent of both the audio track and the vibrations. Here, different types of channels 202, 204, 206 may be created independently of each other without necessarily being derived from the same underlying media content and without necessarily being synchronized in any specific way.

In an embodiment, the multi-sensory media experience file 200 may be stored and/or streamed in an encoded format that does not necessarily separately encode each of the channels 202, 204, 206. Here, an encoded multi-sensory media experience file may include one or more base waveforms together with metadata that includes decoding instructions for generating each of the specific channels from the one or more base waveforms. For example, in some implementations the encoded file may be limited to a stereo audio file and metadata that specifies how the vibroacoustic therapy bed 100 should generate the output channels 204, 206 based on the stereo audio file. The metadata may furthermore specify customizations for applying to the base waveforms that may be derived from information locally stored to a user profile. In this case, the vibroacoustic therapy bed 100 applies the customizations to generate the various channels 202, 204, 206 from the base waveforms. The metadata may furthermore specify customizations that are not necessarily user-specific, but may be based on factors like the geographic location of the vibroacoustic therapy bed 100, the time of day, the day of the week, the season, a hardware, firmware, or software version of the vibroacoustic therapy bed 100, or other factors. In a further example, an encoded multi-sensory media experience file 200 does not necessarily include any base waveforms and may instead include only the metadata. In this case, the various channels 202, 204, 206 may be generated by the vibroacoustic therapy bed 100 directly from the metadata or by obtaining one or more base waveforms from a separate media source as specified by the metadata.

In yet further examples, the multi-sensory media experience file 200 may include additional types of output channels for producing other sensory effects from different types of sensory output devices. For example, the multi-sensory media experience file 200 may include one or more video channels for controlling one or more display devices, one or more olfactory channels for controlling one or more olfactory devices, one or more temperature control channels for controlling one or more heating or cooling elements, or other sensory channels for controlling various other types of output devices.

Figure 3:
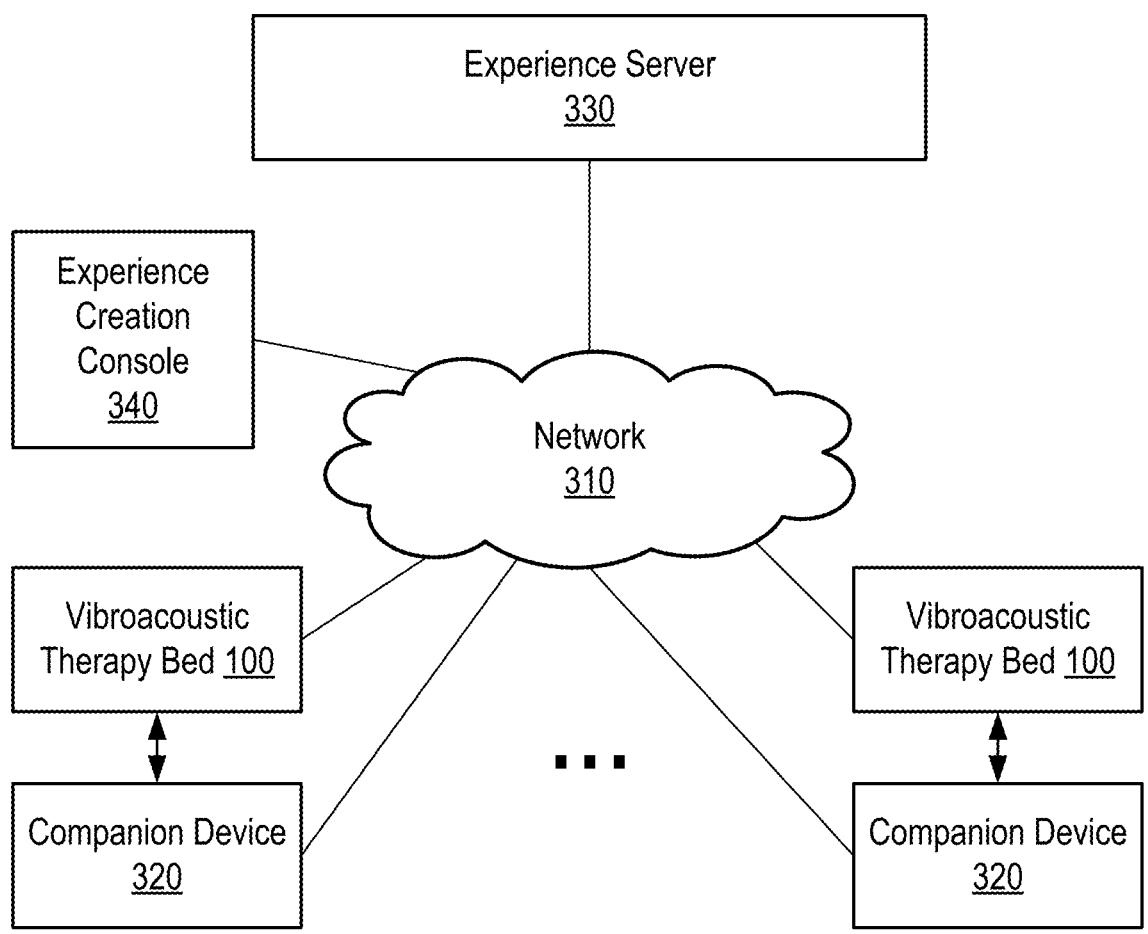
FIG. 3 is an example embodiment of a multi-sensory media streaming environment.

FIG. 3 is a block diagram of a multi-sensory media streaming environment 300 for providing a multi-sensory media experience file 200 to one or more vibroacoustic therapy beds 100 as a streaming service. The multi-sensory media streaming environment 300 comprises an experience server 330, a network 310, a plurality of vibroacoustic therapy beds 100, a plurality of companion devices 320, and an experience creation console 340.

The experience server 330 comprises one or more computing devices for facilitating delivery of multi-sensory media content to one or more of the vibroacoustic therapy beds 100. For example, the experience server 330 may stream multi-sensory media to one or more of the vibroacoustic therapy beds 100 for execution in real-time or near real-time. Such streaming multi-sensory media may be streamed from a preconfigured file stored at the experience server 330 in an on-demand fashion or may be streamed in substantially real-time as the experience is created using an experience creation console 340 as described below. Alternatively, the experience server 330 may store multi-sensory media that can be downloaded to a companion device 320 or vibroacoustic therapy bed 100 for execution at a later time.

The experience server 330 may furthermore store information about the various vibroacoustic therapy beds 100, companion devices 320, and users to facilitate delivery of experiences as a service. For example, the experience server 330 may manage user subscriptions that provide users with access to multi-sensory media experiences available from the experience server 330. For live content, the experience server 330 may concurrently broadcast a multi-media experience to multiple vibroacoustic therapy beds 100 at distributed remote locations. In other situations, different users may independently select on-demand content available from the experience server 330, in which case the experience server 330 may concurrently deliver different user-selected content to different vibroacoustic therapy beds 100 in an on-demand fashion.

In some embodiments, the experience server 330 may facilitate interactions between different users during a multi-sensory media experience. For example, the experience server 330 may facilitate communication of messages between users that are concurrently participating in an experience. Furthermore, the experience server 330 may facilitate exchange of metadata that may affect customizations to the multi-sensory media experience to enable one user's configured preferences to affect the experience of another user.

The companion device 320 comprises a mobile device, a tablet, a laptop computer, a personal computer, a gaming console, a smart television, or other connected computing device that executes an application for interacting with a linked vibroacoustic therapy bed 100 to facilitate a multi-sensory media experience. The companion device 320 may provide a user interface that enables a user to perform actions such as selecting between different multi-sensory media experiences, customizing a multi-sensory media experience, viewing information about a multi-sensory media experience, configuring features of the vibroacoustic therapy bed 100, configuring or viewing a user profile, configuring or viewing account information, or performing other functions associated with operation of the vibroacoustic therapy bed 100. In some instances, a single companion device 320 can interoperate with multiple vibroacoustic therapy beds 100. Furthermore, multiple different companion devices 320 may be paired with a common vibroacoustic therapy bed 100 (e.g., to enable different members of a household to use their individual companion device 320 with a shared vibroacoustic therapy bed 100). In an alternative embodiment, the companion device 320 may be integrated with the vibroacoustic therapy bed 100 and is not necessarily a separate device.

The experience creation console 340 comprises a computing device executing an application that enables creation, modification, and viewing of multi-sensory media experience files that can be executed on one or more vibroacoustic therapy beds 100. For example, the experience creation console 340 provides interfaces and tools for selecting components of an experience (such as music, sounds, vibration patterns, light patterns), arranging the timing of the various components, and for configuring various parameters associated with the components (e.g., intensity, effects, etc.). In an embodiment, the experience creation console 340 may include an editor in the form of a graphical user interface that enables a creator to utilize visual tools to generate the multi-sensory media experience in an intuitive manner. For example, the interface may include a set of tracks corresponding to different channels of the multi-sensory media experience with visual indicators to show the timing of different sensory effects on each track.

The experience creation console 340 may enable creation of multi-sensory media experiences in either an offline or online manner. In an offline creation, the experience creation console 340 facilitates the complete creation of the multi-sensory media experience and stores it to a multi-sensory media experience file (which may be in an encoded form) prior to distributing the experience to a vibroacoustic therapy bed 100. In an online creation, the experience creation console 340 facilitate real-time creation and distribution of the multi-sensory media experience to subscribed vibroacoustic therapy beds 100. In the online creation, the experience is generated live and streamed to the vibroacoustic therapy beds 100 as it is being created. Thus, for example, when the creator inserts a particular sensory effect into the experience creation console 340, that effect is communicated to and executed by any subscribed vibroacoustic therapy beds 100 in substantially real-time.

In an embodiment, users may have access to an experience creation console 340 to enable users to create experiences that are shared to the experience server 330 and may be accessible to other users. Here, depending on the user's certifications, user-created experiences may be directly shared and made accessible to other users or may first go through an approval process before becoming available as a shared multi-sensory media experience.

The network 310 may include any combination of local area networks (LANs), wide area networks (WANs), personal area networks (PANs) or any other multi-point or direct communication links. Furthermore, different portions of the network 310 may utilize wired communication protocols, wireless communication protocols, or a combination thereof. For example, in one implementation, a companion device 320 and a corresponding vibroacoustic therapy bed 100 at a common physical location may be directly connected via Bluetooth, a wireless LAN, or a wired connection. In this case, either the vibroacoustic therapy bed 100 or the companion device 320 (but not necessarily both) may communicate with the experience server 330 via the WAN and may relay communications to the other device via a local connection. In other implementations, both the vibroacoustic therapy bed 100 and the companion device 320 may communicate directly with the experience server 330 via the WAN.

Figure 4:
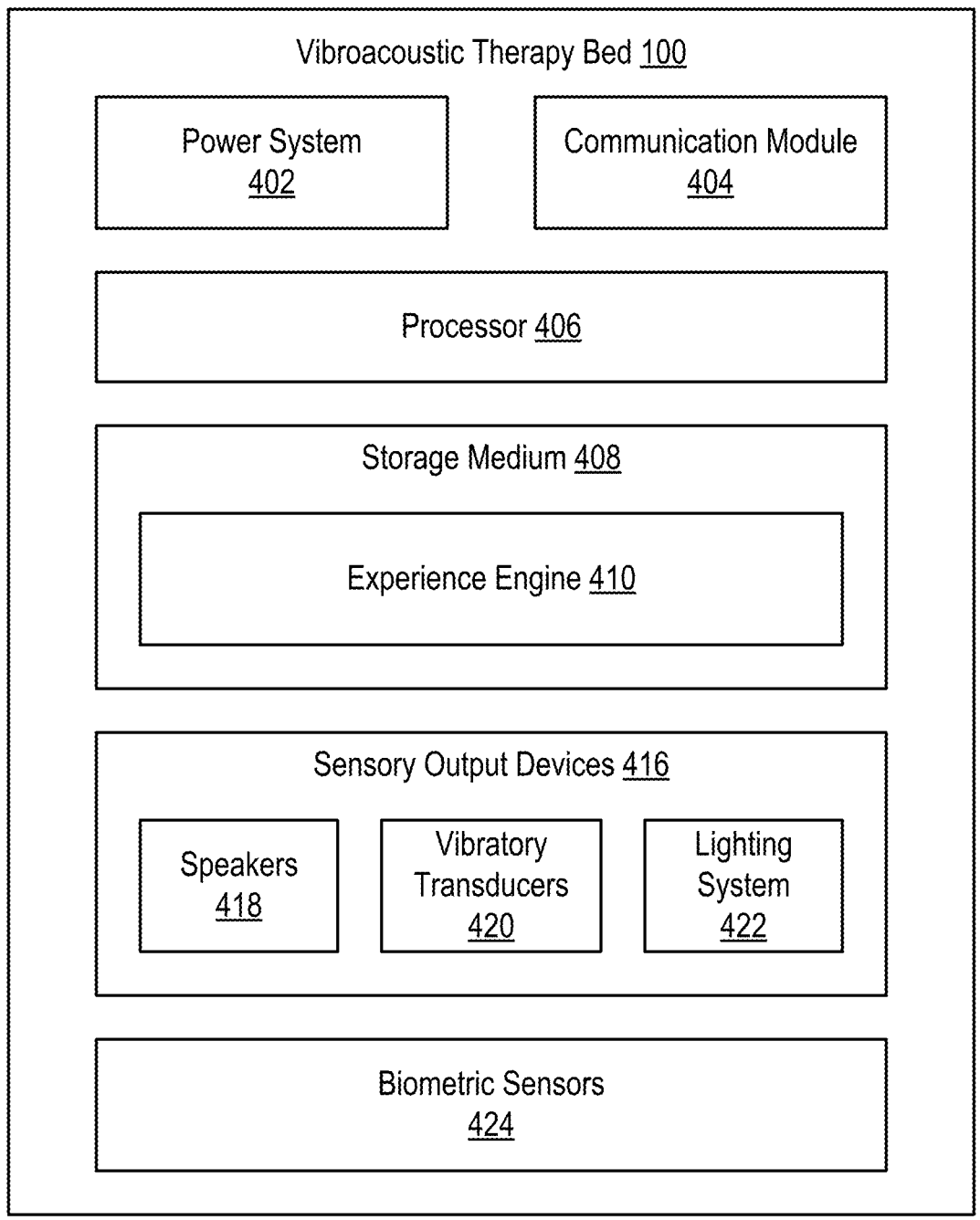
FIG. 4 is a block diagram illustrating an example embodiment of a vibroacoustic therapy bed.

FIG. 4 is a block diagram illustrating an example embodiment of the electronic components of a vibroacoustic therapy bed 100. The vibroacoustic therapy bed 100 comprises a power system 402, a communication module 404, a processor 406, a storage medium 408, sensory output devices 416 (including speakers 418, vibratory transducers 420, and lighting systems 422), and biometric sensors 424.

The power system 402 supplies power to the various electronic components of the vibroacoustic therapy bed 100. The power system 402 may include a conventional power adapter for powering the vibroacoustic therapy bed 100 from an AC power source, one or more batteries, or a combination thereof. The power system 402 may furthermore include a power distribution network for distributing power to various components at different physical positions in the vibroacoustic therapy bed 100.

The communication module 404 interfaces with one or more external devices via the network 310 such as the companion device 320, the experience server 330, other vibroacoustic therapy beds 100, or other connected devices. The communication module 404 may utilize wired or wireless communication technologies or a combination thereof. In an embodiment, the communication module 404 utilizes encrypted communication technologies for all data or for sensitive data such as user profile data and biometric data.

The storage medium 408 may include a non-transitory computer-readable storage medium that stores data relevant to operation of the vibroacoustic therapy device 100 and stores instructions executable by the processor 406 for carrying out functions of the vibroacoustic therapy bed 100 described herein. The storage medium 408 and processor 406 may each comprise single physical devices or may include multiple devices (e.g., multiple storage mediums 408 and multiple processors 406) that may be distributed at different physical locations within in the vibroacoustic therapy bed 100. In one embodiment, the vibroacoustic therapy bed 100 comprises a main processor and main storage medium, and may also include a set of distributed processors and distributed storage mediums. For example, a main base element 110 may include the main processor and main storage medium while other base elements 110 may each include a local processor and local storage medium that each locally control functions associated with the respective base elements 110.

In an embodiment, the storage medium 408 stores an experience engine 410 that controls operation of the vibroacoustic therapy bed 100. For example, the experience engine 410 may control the sensory output devices 416 in accordance with the selected multi-sensory media experience file 200. The experience engine 410 may furthermore collect and process sensed data from the biometric sensors 424. As described in further detail below, the experience engine 410 may adapt the multi-sensory media experience to customize it to a specific user based on user profile data, the sensed biometric data, or other information obtained by the experience engine 410. Further description of the experience engine 410 is provided below with respect to FIG. 4. In alternative embodiments, all or some of the functions attributed to the experience engine 410 may be carried out on the companion device 320 or on the experience server 330 instead of being executed locally on the vibroacoustic therapy bed 100.

The sensory output devices 416 include a set of devices controlled by the experience engine 410 to provide sensory outputs that can be perceived by the user during a multi-sensory media experience. The sensory output devices 416 may include speakers 418, vibratory transducers 420, lighting systems 422, or other output devices for producing the multi-sensory media experience. In different configurations, the sensory output devices 416 may be physically distributed throughout the vibroacoustic therapy bed 100 in different ways. For example, in one configuration, the speakers 418 may be built into a base element 110 near the user's head. Alternatively, the speakers 418 may be embodied as headphones that are physically separate from the vibroacoustic therapy bed 100 and communicatively coupled to the vibroacoustic therapy bed 100 or companion device 320. Furthermore, each base element 110 may include one or more vibratory transducers 420 for delivering vibrations to different parts of the body. Lighting systems 422 may similarly be distributed at different physical locations in the vibroacoustic therapy bed 100 to provide visual stimulus associated with the multi-sensory media experience. In different embodiments, different base elements 110 may include different combinations of sensory output devices 416 including other types of sensory output devices 416 not shown in FIG. 4.

The biometric sensors 424 may include various sensing devices to sense environmental conditions associated use of the vibroacoustic therapy bed 100. For example, the biometric sensors 424 may include devices for sensing weight, heart rate, breathing rate, blood pressure, temperature, movement, audible voice, or other aspects of the user. The biometric sensors 424 may sense these conditions directly or may sense other data from which the relevant conditions can be derived or estimated. For example, the biometric sensors 424 may comprise devices such as pressure sensors, temperature sensors, accelerometers, gyroscopes, cameras, microphones, or other devices that capture different types of raw sensor data from which desired biometric information can be estimated.

Figure 5:
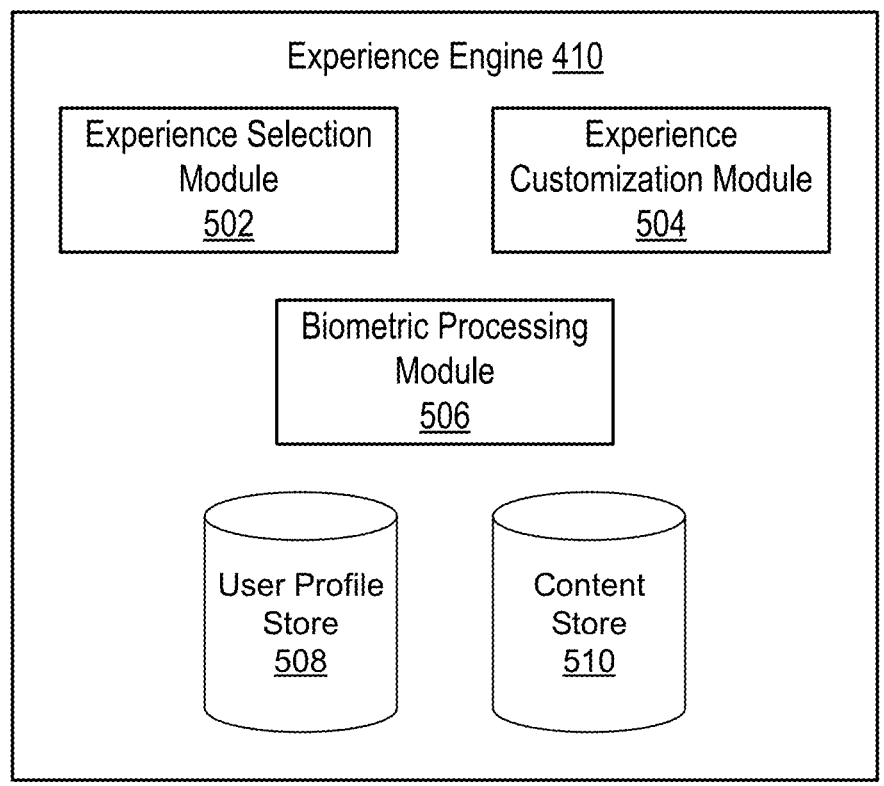
FIG. 5 is a block diagram illustrating an example embodiment of an experience engine.

FIG. 5 illustrates an example embodiment of an experience engine 410. The experience engine 410 comprises an experience selection module 502, an experience customization module 504, a biometric processing module 506, a user profile store 508, and a content store 510.

The experience selection module 502 provides an interface for enabling a user to select a multi-sensory media experience. The experience selection module 502 may enable selection between locally stored experiences, on-demand streaming experiences, or live streaming experiences. Furthermore, in some instances, the experience selection module 502 may provide interface tools to enable a user to create their own customized experience. In further embodiments, the experience selection module 502 may automatically generate recommendations for an experience targeted to a specific user based on information in the user profile store 508, real-time biometric information obtained from the biometric processing module 506, or other data.

The experience customization module 504 customizes a selected experience for a user based on information in the user profile store 508, real-time biometric information obtained from the biometric processing module 506, contemporaneously obtained user inputs, or other data. The experience customization module 504 may tailor a generic multi-sensory media experience to one specifically suited to the user. For example, the experience customization module 504 may apply a set of user-customizable filters to generate or modify the various channels associated with the multi-sensory media experience for driving different output devices 416 of the vibroacoustic therapy bed 100. These filters may control how the channels are generated from one or more base waveforms, the relative intensities for driving the different channels, different effects that may be inserted in the media experience, or other parameters.

In an example customization, a user profile may specify a mapping between different frequency bands of an audio input and each of the output channels. Here, the experience customization module 504 may receive a base waveform associated with the selected media experience, divide the base waveform into a set of frequency bands, and map the frequency bands to different output channels. For example, low frequency components of an audio input may be mapped to a vibration channel that drives a vibrational transducer 420 positioned near the feet while middle frequency components of an audio input may be mapped to a vibrational channel that drives a vibrational transducer positioned near the head. Furthermore, a combination of low and high frequency components may be mapped to the lighting channels to drive different lighting systems 422. Furthermore, the user profile may dictate the relative intensities for driving each of the channels.

In another example customization, the experience customization module 504 may receive a multi-sensory media experience file that references multiple audio clips (or identifies such clips from a user profile). The experience customization module 504 may then map different clips to different output channels according to information specified in the metadata or according to user preferences. For example, the customization module 504 may map a clip associated with bird sounds to output channels driving speakers 418 or other output devices 416 located near the head, while mapping to a clip of ocean sounds to output channels driving vibratory transducers 420 or other output devices 416 located near the feet.

In another example of a user-customization, an experience file may include metadata specifying parameters for inserting user-preferred sounds, music, or other signals into a generic experience file at specified cue points and according to specific parameters. For example, an experience file may include a cue point to insert a user-selected music track or a user-selected sound file at a particular time during the multi-sensory media experience. In this case, the experience customization module 504 reads the metadata, obtains the referenced signals, and inserts the signals into the appropriate output channels in accordance with the metadata specifications.

In yet further examples, the experience customization module 504 performs real-time customization based on sensed biometric inputs from the biometric processing module 506 or based on real-time manual inputs received from the user via a direct user interface, via the companion device 320, via a voice command, or other input mechanism. For example, the intensity or frequency of vibrations may increase or decrease depending on detected biometric conditions in order to invoke a particular result. Here, the experience customization module 504 may apply a machine-learned model or other techniques to generate the outputs. For example, a machine-learned model could map a particular set of sensed inputs to an output configuration that has been learned to increase the user's relaxation.

In another example, the experience customization module 504 may directly generate one or more output channels based on biometric sensing instead of modifying an existing digital waveform. In one use case, a microphone may capture voice outputs and generate output channels directly controlled by the voice outputs. For example, a low frequency voice input may invoke vibrations near the feet while a high frequency voice input may invoke vibrations near the user's head. In other use cases, biometric sensors may capture breathing rate or heart rate and generate vibrations corresponding to the sensed rate. For example, the vibroacoustic therapy bed 100 may initiate vibrations on each inhale, exhale, or both so that the user senses a vibration pattern corresponding to the breathing rate.

The user profile store 508 stores information about a user that can be applied to customize a multi-sensory media experience as described above. For example, the user profile store 508 may store user preferences such as preferred filter configurations for converting audio to a set of sensory output channels used to drive different portions of the vibroacoustic therapy bed 100, a selection of preferred music or sound clips for integrating into a multi-sensory media experience, preferred intensity levels for driving different channels of the vibroacoustic therapy bed 100, or other user preferences.

The content store 412 stores content that can be used to generate and customize a multi-sensory media experience. For example, the content store 412 may store music, sound clips, vibration patterns, light patterns, visual or audio effects, or other media content that can be incorporated into a multi-sensory media experience using any of the techniques described herein.

While FIG. 4 illustrates the experience engine 410 as a component of the vibroacoustic therapy bed 100, in alternative embodiments, all or some of the modules of the experience engine 410 may instead be stored and/or executed on the companion device 320, on the experience server 330, or on some combination of devices.

Figure 6:
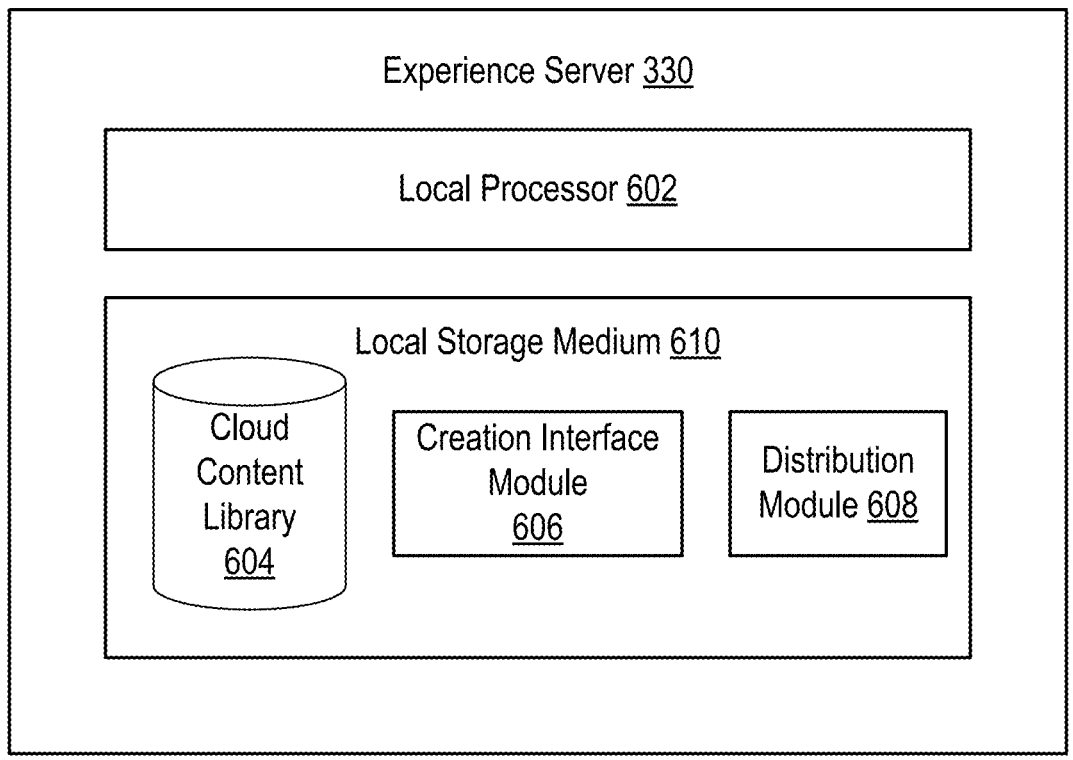
FIG. 6 is a block diagram illustrating an example embodiment of an experience server.

FIG. 6 is a block diagram illustrating an example embodiment of an experience server 330. The experience server 330 includes a processor 602 and a storage medium 610 storing a cloud content library 604, a creation interface 606, and a distribution module 608. In alternative embodiments, all or part of the modules of the experience engine 410 described above could alternatively be incorporated in the experience server 330.

The cloud content library 604 stores multi-sensory media experience files and other content that can be used to generate or customize a multi-sensory media experience. For example, the cloud content library 604 may store multi-sensory media experience files that are available for on-demand streaming or download. The cloud content library 604 may furthermore store media elements such as music, sound clips, vibration patterns, light patterns, visual or audio effects, or other media content that can be incorporated into a multi-sensory media experience using any of the techniques described herein.

The creation interface module 606 interfaces with the experience creation console 340 to facilitate creation or modification of multi-sensory media experiences for storage to the experience server 330 or for live streaming. For example, the creation interface module 606 may provide web-based interfaces and tools (e.g., an editor) used by the experience creation console 340 to create a multi-sensory media experience. The creation interface module 606 may furthermore provide access to the cloud content library 604 to enable stored content to be incorporated into experiences.

The creation interface module 606 may be accessed by professional creators that may create live or on-demand multi-sensory media experiences. Furthermore, the creation interface module 606 may enable users to create their own multi-sensory media experiences for their own use or for sharing with other users. Here, for example, users can select between various content in the cloud content library 604 for incorporating into an experience. In an example, a user may select a set of audio clips from the cloud content library 604 for incorporating into an experience. The creation interface module 606 may then automatically generate the experience based on the selected clips. Here, the creation interface module 606 may determine a mapping of selected clips to corresponding channels based on user preferences, metadata associated with the clips, or direct user input. The user could also choose to have these mapping change over time so different audio clips become mapped to different channels over the course of the experience. Multi-sensory media experiences that are created using the creation interface module 606 may then become accessible for download or streaming by other users.

The distribution module 608 facilitates distribution of multi-sensory media experiences to the vibroacoustic therapy beds 100. As described above, distribution may occur as a live stream, as an on-demand stream, or as a download.

In alternative embodiments, aspects of the experience server 330 including the cloud content library 604, the creation interface module 606, and the distribution module 608 may execute locally on a vibroacoustic therapy bed 100 or a companion device 320 instead of on a server 330. Here, for example, the creation interface module 606 may be embodied as a local application that lets a user locally create multi-sensory media experiences without necessarily having to access a server. Furthermore, in some embodiments, multi-sensory media experiences may be distributed directly by a local distribution module 608 via a peer-to-peer connection without necessarily having to go through a server 330.

Figure 7:
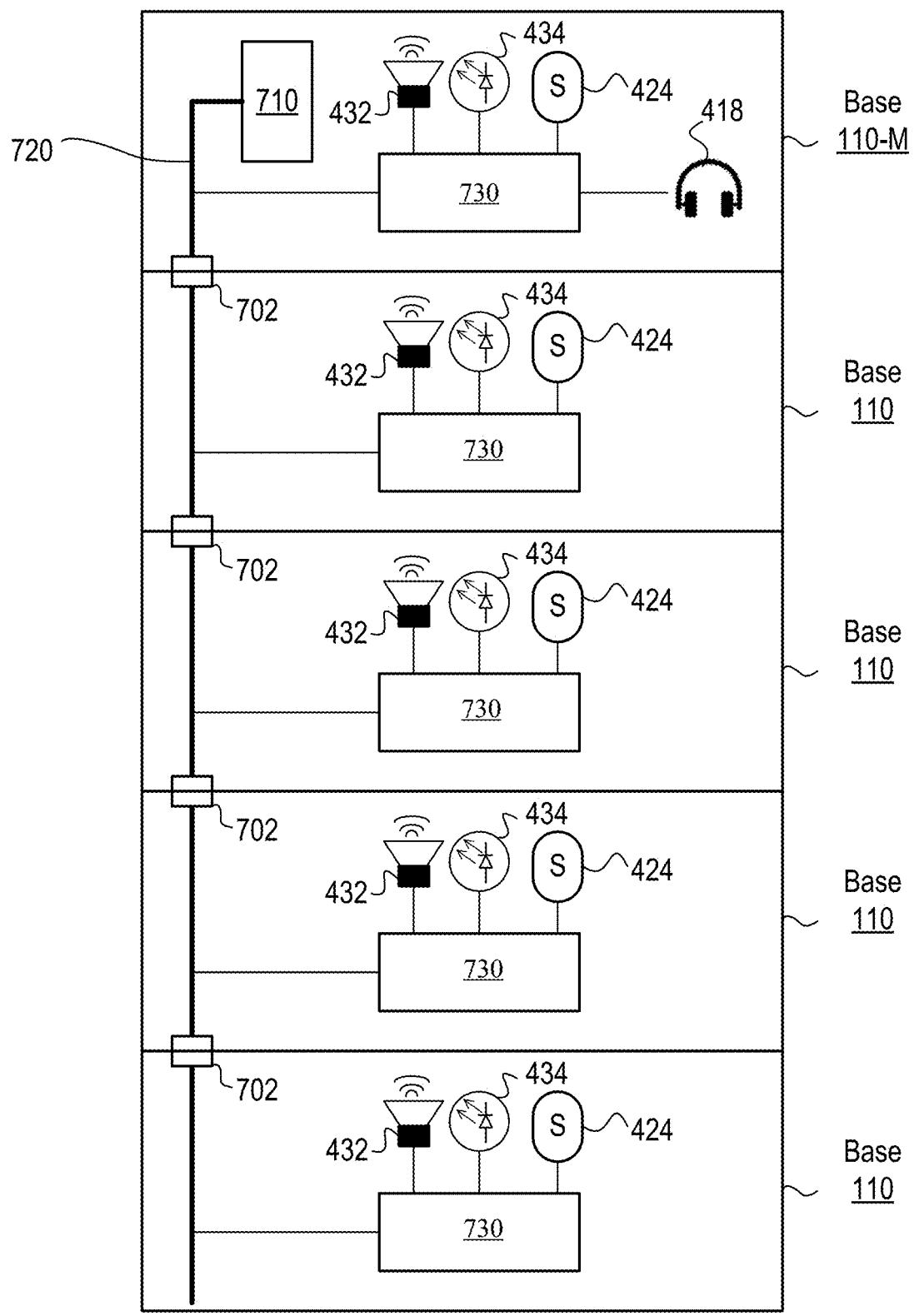
FIG. 7 is an example electronics layout for a vibroacoustic therapy bed.

FIG. 7 illustrates an example embodiment of an electronics layout of a vibroacoustic therapy bed 100. In this example, the vibroacoustic therapy bed 100 comprises a set of five base elements 110 that are physically coupled together by a set of physical connectors and are electronically connected by electronic connectors 702. A main base element 110-M includes a main controller 710 coupled to a bus 720 that electrically connects to electronics in each of the base elements 110. Each base element 110 also includes a local controller 730 coupled to the bus 720. The local controllers 730 each facilitate local control of a set of sensory output devices (e.g., headphone speakers 418, vibratory transducers 432, lighting system 434, or other sensory output devices) and/or biometric sensors 424 integrated with that base element 110.

The main controller 710 may be responsible for high-level control functions of the vibroacoustic therapy bed 100. For example, the main controller 710 may include the communication module 404 and execute at least a subset of the functions of the experience engine 410. In an example scenario, the main controller 710 may receive an experience file, perform processing of the file to customize the multi-sensory media experience for the user, and distribute the multi-sensory media experience to the distributed controllers 730 via the bus 720. The local controllers 730 may perform additional processing on the received signals and drive the respective sensory output devices 418, 432, 434 accordingly. The local controllers 730 may furthermore perform processing of sensor data obtained from the local biometric sensors 324 and output the sensor data on the bus 720 to the main controller 710. The main controller 710 may perform additional processing of the sensor data and may update the multi-sensory media experience responsive to the processed sensor data as described above.

In different embodiments, the set of channels for driving the sensory output devices 418, 432, 434 may be generated by the main controller 710, the local controllers 730, or a combination thereof. For example, in one implementation, the main controller 710 sends one or more input waveforms to the local controllers 730 via the bus 720 together with sets of filtering parameters for applying by each local controller 730. The local controllers 730 each apply their respective filtering parameters to generate their respective channels to drive the locally connected output devices 432, 434, 418. The filtering parameters applied at each local controller 730 may be different to invoke different sensations at different physical locations derived from the same set of one or more input waveforms.

In another implementation, the main controller 710 applies a set of filters (controlled by different filter parameters) to generate the set of channels that are each targeted to the different sensory output devices of the different base elements 110. The main controller 710 may transmit the channels on the bus 720 together with address information associated with each channel. The individual local controllers 730 read the data on the bus 720 and detect data associated with their respective addresses. The local controllers 730 then obtain the relevant channel data and drive their respective output devices accordingly. In some embodiments, the local controllers 730 may perform additional signal processing on the locally received data associated with their respective channels. For example, signal processing such as equalization or additional filtering may be performed by the local controllers 730 in addition to filtering performed by the main controller 710.

In yet another implementation, the main controller 710 and local controllers 730 may operate together to generate the channels. In one embodiment, the main controller 710 processes one or more input waveforms to generate a set of pre-processed waveforms. For example, the main controller 710 may apply a set of bandpass filters to a digital audio input to divide the digital audio input into a set of pre-processed waveforms each corresponding to a different frequency band. The pre-processed waveforms are then sent on the bus 720 to the local controllers 730. The local controllers 730 then apply local filtering parameters to each select one or more of the pre-processed waveforms and generate the respective channels for driving the output devices from the selected pre-processed waveforms. In this example implementation, the local controllers 730 do not necessarily perform complex signal processing and can therefore operate with lower processing power and memory resources than the main controller 710.

Figure 8:
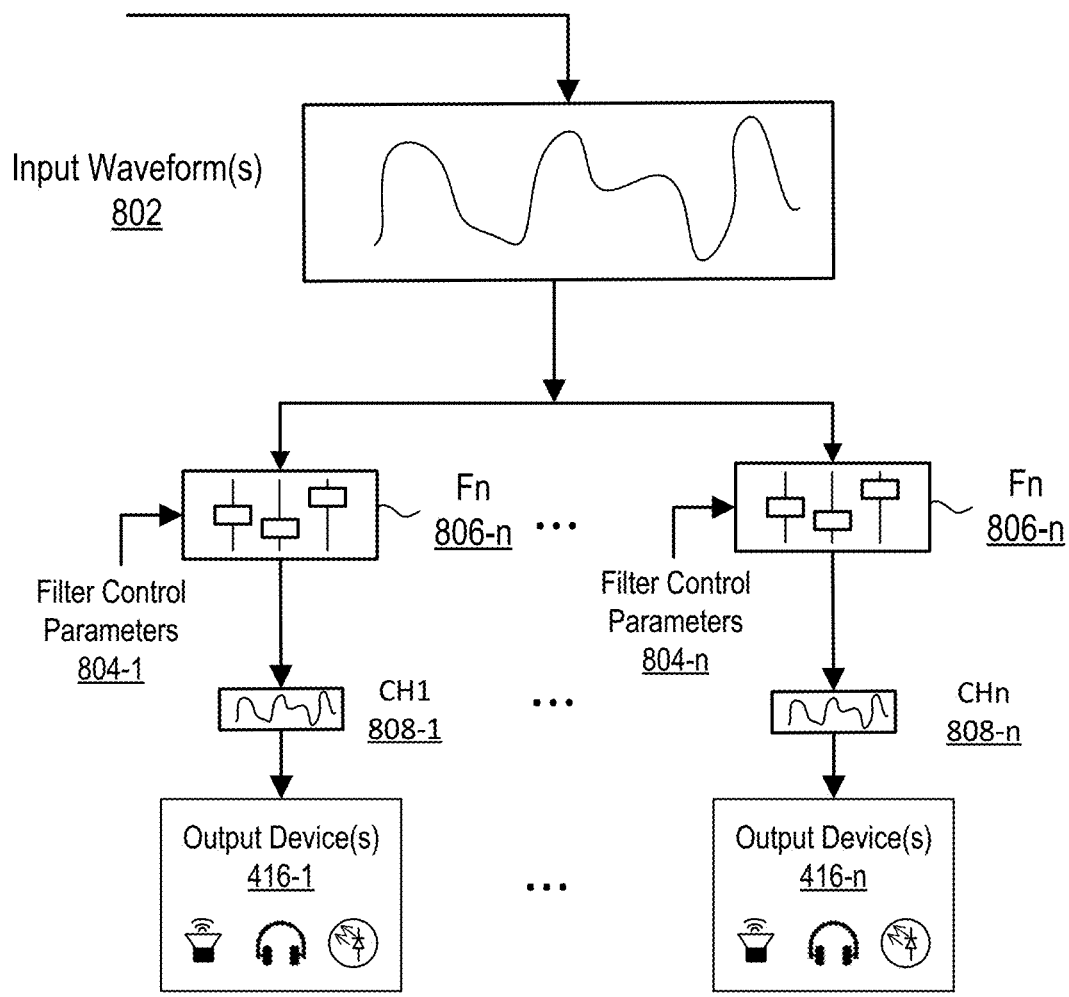
FIG. 8 is a diagram illustrating an example process for driving a set of sensory output devices from one or more input waveforms in a vibroacoustic therapy bed.

FIG. 8 is a diagram illustrating an example technique for generating a plurality of channels for driving a vibroacoustic therapy bed 100 based on one or more input waveforms 802. The input waveforms 802 may comprise, for example, a time-localized clip of a music file, spoken word audio, a sound clip, or a signal representing a lighting pattern, a vibration pattern, biometric data, another signal for driving a particular type of sensory output device, or a combination thereof. The input waveforms 802 may be obtained from a file or may be obtained in real-time (e.g., as audio captured by a microphone or as other sensor data captured by biometric sensors). A set of filters (F1, . . . , Fn) 806 are applied to the input waveforms 802 to generate to a set of output channels (CH1, . . . , CHn) 808 that drive respective output devices 416. Here, each channel 808 may drive a single output device 416 or may drive multiple output devices 416 of the same or different types. As described above, the filters 806 may be implemented in either the main controller 710, the local controllers 730, or a combination thereof.

The filters 806 are each independently customizable based on respective filter control parameters 804 that may be derived from metadata associated with a multi-sensory media experience file, user preferences, biometric data, or a combination thereof. In one example, a filter 806 may be configured as a source-selection filter that selectively passes one or more of the input waveforms 802 to its respective channel. For example, if the input waveforms 802 include a dedicated light pattern signal, a filter 806 associated with a channel 808 driving a lighting system 422 may be configured to pass only the light pattern signal. Furthermore, if the input waveforms 802 include a vibration pattern signal intended for driving a specific transducer 420 located near the mid-back, the filter 806 associated with the channel 808 driving that specific transducer 420 may be configured to pass the corresponding vibration pattern signal.

In other instances, the input waveforms 802 do not necessarily have dedicated signals targeted to specific channels 808. In such cases, the filters 806 may be configured to generate their respective channel 808 from the existing input waveforms 802. For example, if the input waveform 802 includes only a stereo audio file, the filters 806 for channels 808 driving the vibratory transducers 420 and lighting systems 422 may generate their respective channels 808 based on the audio file in a manner specified by the filter control parameters 804.

In one example configuration, the filters 806 may operate as bandpass filters that are each configured to pass a specific frequency band of an input waveform 802 to their respective channels 808. For example, a first channel driving a vibratory transducer 420 near the feet may be configured to pass frequencies associated with a first frequency range (e.g., a very low frequency range), while a second channel driving a vibratory transducer 420 near the mid-back may be configured to pass frequencies associated with a second frequency range (e.g., a high frequency range). In other instances, a filter 806 can pass multiple different selected frequency bands to its respective channel 808. The mapping of frequency bands to channels 808 may be based on the user's specific preferences or based on metadata associated with the input waveform 802.

The filter control parameters 804 may furthermore specify different audio processing functions applied by different filters 806 when generating their respective channels 808. For example, the filter control parameters 804 may specify amplitude adjustments, frequency shifts, phase shifts, or other effects for applying to the input waveform 802 to generate the specific channel 808. Here, for example, the filter control parameters 804 can operate to equalize the channels 808 such that, for example, vibrations outputted near the user's feet have a large gain while vibrations outputted near the head have a much smaller gain.

In a further example, the filter control parameters 804 can cause the filters 806 to operate as dynamic filters that change their signal processing parameters over time according to some specified sequence. For example, a particular filter 806 may be configured to vary the gain applied to its channel 808 over time according to a sinusoidal function or other function. These types of dynamic filtering effects enable the vibroacoustic therapy bed 100 to control the different output devices 416 in a coordinated way to achieve certain desired effects. For example, by dynamically varying the gain applied to vibrations outputted at different locations along the length of the vibroacoustic therapy bed 100 according to a sinusoidal function, a wave sensation can be achieved.

In a further example, the filters 806 may include multiple layers of filters that serially process the input waveforms 802. For example, a first set of filters 806 may be implemented by the main controller 710 to generate the preprocessed waveforms, followed by a second set of filters implemented by the local controllers 730 to generate the output channels 808.

Figure 9:
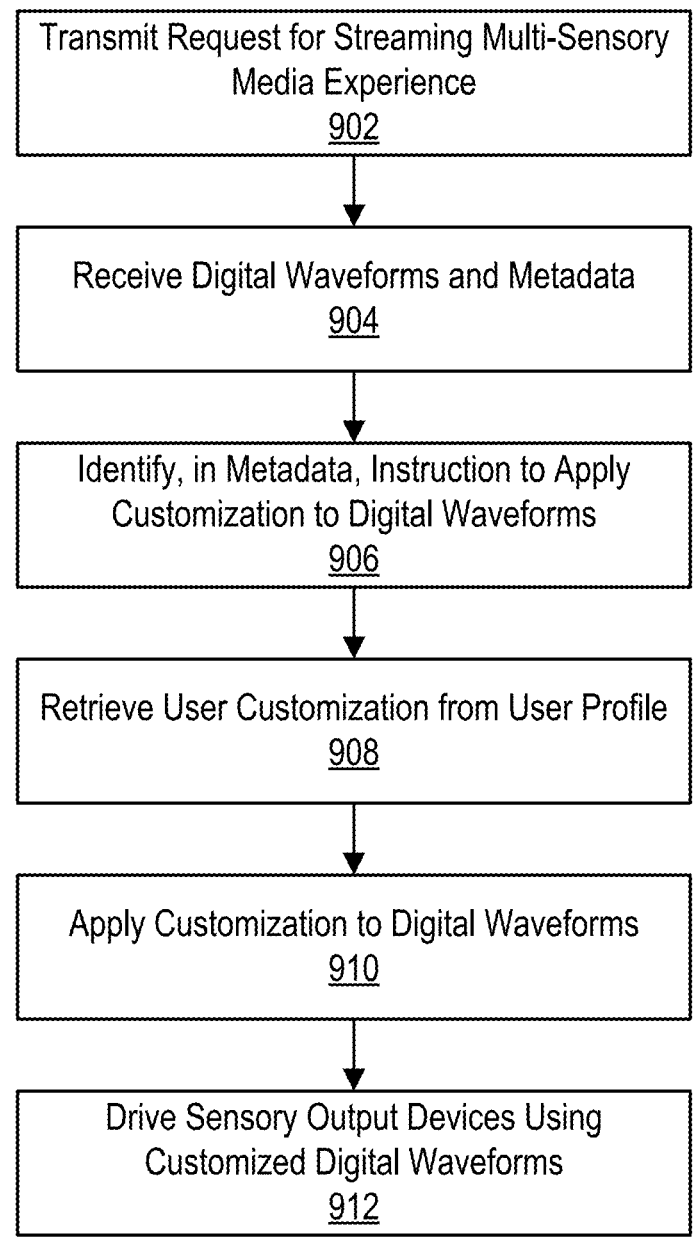
FIG. 9 is a flowchart illustrating an example embodiment of a process for streaming a multi-sensory media experience.

FIG. 9 is a flowchart illustrating an example process for providing a streaming multi-sensory media experience. A request for a streaming multi-sensory media experience is transmitted 902 to the experience server 330 from the vibroacoustic therapy bed 100 or companion device 320. In response to the request, the experience server 330 streams the multi-sensory media experience file to the vibroacoustic therapy bed 100 (either directly or via the companion device) and the vibroacoustic therapy bed 100 receives 904 the multi-sensory media experience file. The multi-sensory media experience file may be streamed to the vibroacoustic therapy bed 100 for real-time playback or may be stored locally for playback at a later time. The experience file includes at least one digital waveform (e.g., digital audio and/or other dedicated sensory output channels) and includes metadata associated with the digital waveforms.

The experience engine 410 identifies 906, from the metadata, decoding instructions for applying one or more user customizations to the digital waveforms. The experience engine 410 obtains 908 the customization data from the user profile and applies 910 the customization data to the digital waveforms to generate user-customized digital waveforms. Here, the customization data may include filter control parameters for controlling filters applied to the digital waveforms to generate the sensory output channels. For example, the filter control parameters may cause each filter to select between different digital waveforms, select specific frequency bands of the digital waveforms, apply equalization to the digital waveforms, insert sounds or other effects into the digital waveforms, or perform other functions. In this way, the experience engine 410 generates a plurality of sensory output channels for diving different sensory output devices 416 of the vibroacoustic therapy bed 100 customized to specific user preferences. The vibroacoustic therapy bed then drives 912 a set of sensory output devices 416 (e.g., vibrational transducers 420, speakers 418, lighting systems 422, or other output devices) at different positions along a length of the vibroacoustic therapy bed 100 according to the user-customized digital waveforms.

Figure 10:
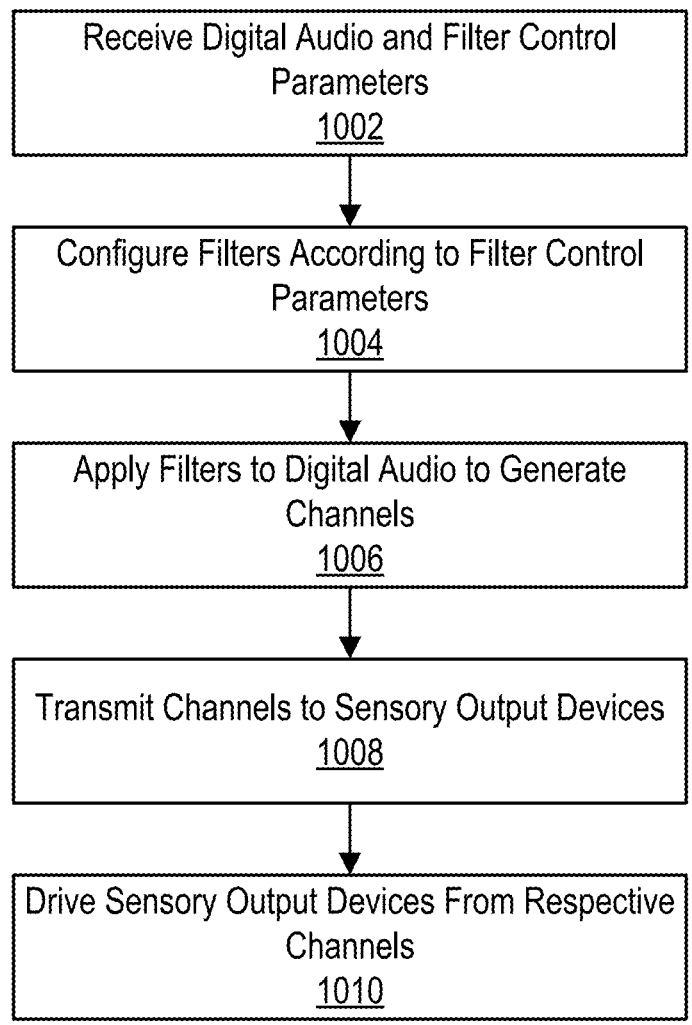
FIG. 10 is a flowchart illustrating an example embodiment of a process for generating a set of channels for driving sensory output devices of a vibroacoustic therapy bed derived from a digital audio input.

FIG. 10 illustrates an example embodiment of a process for generating a set of sensory output channels for driving sensory output devices 416 of a vibroacoustic therapy bed 100 from a digital audio input. The experience engine 410 receives 1002 digital audio and a set of filter control parameters (which may be derived from a user profile, from metadata associated with the experience file, or generated based on biometric feedback). The experience engine 410 configures 1004 a set of filters according to the filter control parameters. The experience engine 410 then applies 1006 the filters to the digital audio to generate a set of channels. For example, the filters may generate the channels to each comprise different frequency bands of the digital audio, to apply different gains, and/or to apply other signal processing effects. The channels are then transmitted 1008 to respective sensory output devices 416 integrated into the vibroacoustic therapy bed 100. The vibroacoustic therapy bed 100 drive the sensory output devices 416 based on the respective channels.

Figure 11:
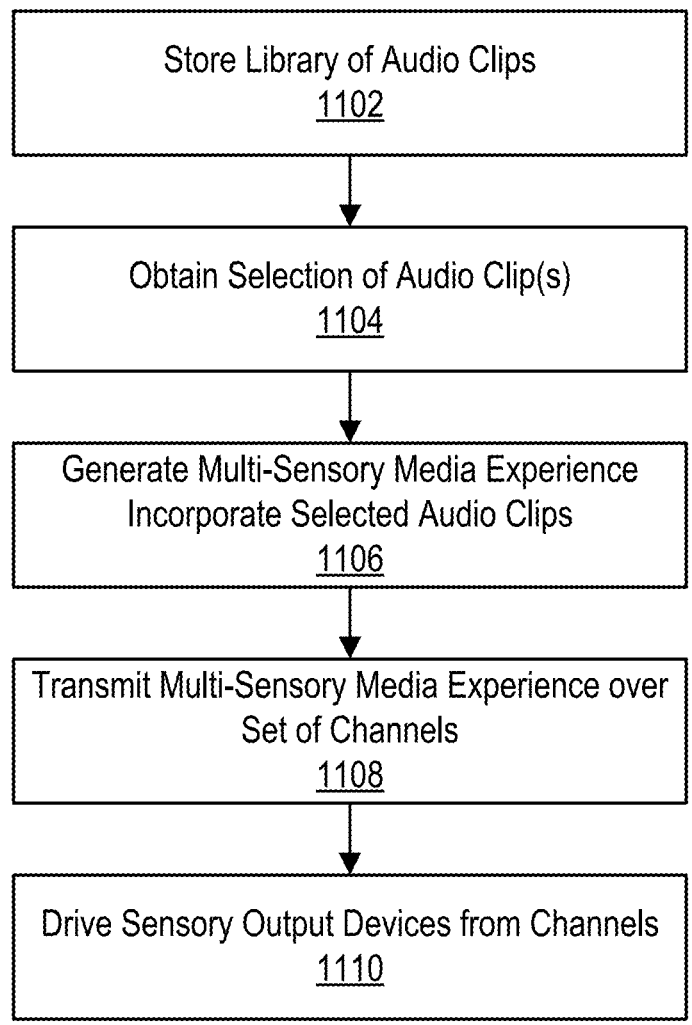
FIG. 11 is a flowchart illustrating an example embodiment of a process for generating a multi-sensory media experience based on a set of user-selected sounds.

FIG. 11 is a flowchart illustrating an example embodiment of a process for driving sensory output devices 416 of a vibroacoustic therapy bed based on a set of sounds from a sound library. The vibroacoustic therapy bed 100 stores 1102 a library of audio clips. Alternatively, the vibroacoustic therapy bed 100 may obtain audio clips from the experience server 330 or the companion device 320. A selection of audio clips is obtained 1104. For example, a user may select to incorporate bird sounds, ocean waves, train sounds, white noise, music, spoken word, or other user-specified sounds in a multi-sensory media experience. Alternatively, the audio clips may be automatically selected based on user preferences or biometric feedback. Furthermore, the audio clips may be selected by an experience creator that is not necessarily the user. The experience engine 410 generates 1106 a multi-sensory media experience that incorporates the selected audio clips. For example, the experience engine 410 may generate playback patterns associated with each of the sounds and may overlay the sounds clips with each other or with background music or spoken word audio. The generated multi-sensory media experience is transmitted 1108 over a set of channels to a set of sensory output devices 416. The vibroacoustic therapy bed 100 drives 1110 the sensory output devices 416 based on the respective channels.

In further alternative embodiments, the techniques, architectures, and processes described above could be implemented in other types of vibroacoustic devices in place of the vibroacoustic therapy bed. Such a device may have the same or similar functional architecture as the vibroacoustic therapy bed 100 of FIG. 4, may be usable in place of the vibroacoustic therapy bed 100 of FIG. 3, and may include similar features to the vibroacoustic therapy bed 100 but have a different form factor that is not necessarily a bed. For example, in an embodiment, such a vibroacoustic device may comprise a vibroacoustic chair instead of a bed. Similar to the vibroacoustic bed 100 described above, the vibroacoustic chair may include integrated vibrational transducers and/or other sensory output devices to produce sensory outputs at different locations of the body based on a set of sensory output channels generated in the same manner described above. In another example, the vibroacoustic device may comprise a bed cover or chair cover that retrofits a conventional bed or chair to enable features described herein. Furthermore the vibroacoustic device may comprise other furniture such as a coach, loveseat, futon, hammock, etc. In other examples, a vibroacoustic device may comprise a body suit or other garment that can be worn by a user. Here, the vibroacoustic garment may include integrated vibrational transducers and/or other sensory output devices to produce sensory outputs at different locations of the body based on a set of sensory output channels generated in the same manner described above. In yet further examples, the vibroacoustic device may comprise a backpack for wearing on a user's back. In further examples, a set of individual garments may be communicatively coupled and operate together to deliver a multi-sensory media experience as described above. For example, the multi-media sensory experience could be delivered by shoes, socks, pants, shorts, shirts, hats, gloves, wearable pads, or other wearable elements that may be physically separate but configured to interoperate to delivery sensory outputs to different physical locations.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a tangible computer readable storage medium or any type of media suitable for storing electronic instructions, and coupled to a computer system bus. Furthermore, any computing systems referred to in the specification may include a single processor or may be architectures employing multiple processor designs for increased computing capability.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

The invention claimed is:

1. A method for providing a multi-sensory experience in a vibroacoustic therapy bed, the method comprising:
   transmitting, to a remote server, a request for a streaming multi-sensory media experience for executing on the vibroacoustic therapy bed;
   responsive to the request, receiving from the remote server, streaming multi-sensory media including digital waveforms and metadata associated with the digital waveforms;
   identifying in the metadata, an instruction to apply user customization data to the digital waveforms;
   retrieving the user customization data from a user profile associated with a user;
   applying the user customization data to the digital waveforms to generate a set of user-customized channels, wherein each user-customized channel of the set is derived from one or more components of the digital waveforms; and
   driving a set of vibrational transducers integrated at different positions of the vibroacoustic therapy bed according to the set of user-customized channels.

2. The method of claim 1, wherein applying the user customization data comprises:
   applying a set of filters obtained from the user profile to the digital waveforms to generate the set of user-customized channels.

3. The method of claim 2, wherein the set of filters generates the set of user-customized channels such that each user-customized channel is limited to one or more frequency bands of the digital waveforms for driving corresponding vibrational transducers of the vibroacoustic therapy bed.

4. The method of claim 2, wherein the set of filters generates the set of user-customized channels by applying a set of user-specified gains to the one or more components of the digital waveforms for driving corresponding vibrational transducers of the vibroacoustic therapy bed.

5. The method of claim 2, wherein the set of filters generates the set of user-customized channels by selecting one or more of the digital waveforms for driving corresponding vibrational transducers of the vibroacoustic therapy bed.

6. The method of claim 1, wherein applying the user customization data comprises:
   obtaining from the user profile, a stored reference to a waveform clip;
   and inserting the waveform clip in the digital waveforms in accordance with the metadata.

7. The method of claim 1, wherein the metadata associated with the digital waveforms includes an instruction to output a specified digital waveform to one of the set of user-customized channels.

8. The method of claim 1, wherein receiving the streaming multi-sensory media comprises:
   streaming from the remote server, a previously stored multi-sensory media experience file.

9. The method of claim 1, wherein receiving the streaming multi-sensory media comprises:
   streaming from the remote server, a live multi-sensory media experience file as the live multi-sensory media experience file is created.

10. The method of claim 1, further comprising:
    driving a set of audio speakers according to the set of user-customized channels.

11. The method of claim 1, further comprising:
    driving a set of light emitters at different positions along a length of the vibroacoustic therapy bed according to the set of user-customized channels.

12. A non-transitory computer-readable storage medium storing instructions for providing a streaming multi-sensory media experience in a vibroacoustic therapy bed, the instructions when executed by a processor cause the processor to perform steps comprising:

transmitting, to a remote server, a request for a streaming multi-sensory media experience for executing on the vibroacoustic therapy bed;

responsive to the request, receiving from the remote server, streaming multi-sensory media including digital waveforms and metadata associated with the digital waveforms;

identifying in the metadata, an instruction to apply user customization data to the digital waveforms;

retrieving the user customization data from a user profile associated with a user;

applying the user customization data to the digital waveforms to generate a set of user-customized channels, wherein each user-customized channel of the set is derived from one or more components of the digital waveforms; and driving a set of vibrational transducers integrated at different positions of the vibroacoustic therapy bed according to the set of user-customized channels.

13. The non-transitory computer-readable storage medium of claim 12, wherein applying the user customization data comprises:

applying a set of filters obtained from the user profile to the digital waveforms to generate the set of user-customized channels.

14. The non-transitory computer-readable storage medium of claim 13, wherein the set of filters generates the set of user-customized channels such that each user-customized channel is limited to one or more frequency bands of the digital waveforms for driving corresponding vibrational transducers of the vibroacoustic therapy bed.

15. The non-transitory computer-readable storage medium of claim 13, wherein the set of filters generates the set of user-customized channels by applying a set of user-specified gains to the one or more components of the digital waveforms for driving corresponding vibrational transducers of the vibroacoustic therapy bed.

16. A vibroacoustic therapy bed for providing a streaming multi-sensory media experience, the vibroacoustic therapy bed comprising:

a processor; and a non-transitory computer-readable storage medium storing instructions that when executed by the processor cause the processor to perform steps comprising:

transmitting, to a remote server, a request for a streaming multi-sensory media experience for executing on the vibroacoustic therapy bed;

responsive to the request, receiving from the remote server, streaming multi-sensory media including digital waveforms and metadata associated with the digital waveforms;

identifying in the metadata, an instruction to apply user customization data to the digital waveforms;

retrieving the user customization data from a user profile associated with a user;

applying the user customization data to the digital waveforms to generate a set of user-customized channels, wherein each user-customized channel of the set is derived from one or more components of the digital waveforms; and driving a set of vibrational transducers integrated at different positions of the vibroacoustic therapy bed according to the set of user-customized channels.

17. The vibroacoustic therapy bed of claim 16, wherein applying the user customization data comprises:

applying a set of filters obtained from the user profile to the digital waveforms to generate the set of user-customized channels.

18. The vibroacoustic therapy bed of claim 17, wherein the set of filters generates the set of user-customized channels such that each user-customized channel is limited to one or more frequency bands of the digital waveforms for driving corresponding vibrational transducers of the vibroacoustic therapy bed.

19. The vibroacoustic therapy bed of claim 17, wherein the set of filters generates the set of user-customized channels by applying a set of user-specified gains to the one or more components of the digital waveforms for driving corresponding vibrational transducers of the vibroacoustic therapy bed.

20. The vibroacoustic therapy bed of claim 16, wherein applying the user customization data comprises:

obtaining from the user profile, a stored reference to a waveform clip; and inserting the waveform clip in the digital waveforms in accordance with the metadata.

* * * * *